United States Patent [19]

Kubota et al.

[11] 4,324,680

[45] Apr. 13, 1982

[54] SILVER-SILVER CHLORIDE ELECTRODE AND MANUFACTURING METHOD THEREOF

[75] Inventors: Misao Kubota, Maruko; Yoshitada Hanai, Ueda; Toshiaki Yamaguchi, Tobu, all of Japan

[73] Assignee: Totoku Electric Co., Ltd., Tokyo, Japan

[21] Appl. No.: 180,428

[22] Filed: Aug. 22, 1980

[51] Int. Cl.³ ............... H01M 4/58; H01M 4/04
[52] U.S. Cl. ................. 252/182.1; 264/61; 429/199; 429/219
[58] Field of Search ............ 252/182.1; 264/61; 429/199, 219

[56] References Cited

U.S. PATENT DOCUMENTS

| | | | |
|---|---|---|---|
| 3,445,296 | 5/1969 | Abe et al. | 429/219 |
| 4,118,552 | 10/1978 | Chireau et al. | 429/219 |
| 4,125,689 | 11/1978 | Jumel | 429/219 |
| 4,187,328 | 2/1980 | Jumel | 429/219 |

*Primary Examiner*—Benjamin R. Padgett
*Assistant Examiner*—Irwin Gluck
*Attorney, Agent, or Firm*—Oblon, Fisher, Spivak, McClelland & Maier

[57] ABSTRACT

A silver-silver chloride electrode used for medical measurement etc. and its manufacturing method are disclosed. A method of manufacturing a silver-silver chloride electrode by chemically reacting silver powder with chlorine in a solution containing chlorine ions or in a gas mixture containing chlorine or a chlorine compound to form silver chloride on the surface of the silver powder, followed by compression-forming of said powder is disclosed together with the silver-silver chloride electrode obtained by said method.

8 Claims, 3 Drawing Figures

SILVER-SILVER CHLORIDE ELECTRODE AND MANUFACTURING METHOD THEREOF

BACKGROUND OF THE INVENTION

The present invention relates to a silver-silver chloride electrode suitable as an electrode for detecting electrical signals from living bodies and as a standard electrode for measuring electrical characteristics, and the method for manufacturing thereof.

Conventionally, electrodes such as silver, nickel silver, copper and Sunplatina electrodes have been used as sensors to detect low level electrical signals at the skin surface of a living body. These electrodes are not satisfactory since the electrode potential is apt to vary with various secreted substances, temperature and humidity of the environment. Further, the electrodes are easily influenced by external noise. To overcome these problems, non-polarizing electrodes such as silver-silver chloride electrode which are more electrochemically stable than conventional electrodes have recently been used. As a manufacturing method of this electrode, generally a method is used in which silver chloride is deposited by electroplating in a solution containing chlorine ions such as a sodium chloride solution, or another method is used in which silver powder and silver chloride powder are mixed mechanically and then formed by compression. However, the former method has difficulty in manufacture due to the need for very precise plating conditions and long treating time for obtaining an electrode of high performance, as well as the drawback that the resultant silver chloride layer is mechanically brittle and apt to peel off. The latter method has the following drawbacks: Because silver powder and silver chloride powder are mixed in a simple proportion by mere mechanical blending, not only are many process steps such as weighing, blending, pressure-forming, and heat treatment necessary, but also fully homogeneous mixing of both components is not easy due to the difference in specific gravity and particle size, etc., between silver powder and silver chloride powder. This often causes nonuniform local deposition of silver chloride in the porous silver matrix, resulting in unstable quality. The silver powder to be used must be a more expensive reduced silver powder. This reduced silver powder has generally small particle size, tends to cause losses by sticking to the container wall, is cumbersome in handling, and has many problems in manufacture. Furthermore, the heat treatment necessary to obtain an electrode of stable characteristics requires precise temperature control, otherwise the characteristics will fluctuate.

SUMMARY OF THE INVENTION

The present invention has been made to overcome these problems of the prior art and has for its object to provide a silver-silver chloride electrode of low polarization characteristic and small potential variation providing a stable electrode potential in a short period. It is another object of the present invention to provide a method for manufacturing a silver-silver chloride electrode with uniform product quality in a simple process.

To the above and other ends, the present invention provides a silver-silver chloride electrode characterized by forming 0.05–80% by weight of silver chloride on the surface of silver powder particles, followed by pressure-forming said compound powder.

The present invention further provides a method for manufacturing a silver-silver chloride electrode which comprises the steps of chemically reacting silver powder particles with chlorine in a solution containing chlorine ions or in a gas mixture containing chlorine or a chlorine compound to form silver chloride on the surface of the silver powder particles, and molding the resultant silver-silver chloride compound powder into a desired shape by compression.

DETAILED DESCRIPTION OF THE PREFERRED EMBODIMENTS

Figure 1:
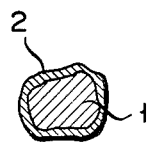
FIG. 1 is an enlarged sectional view representing a silver-silver chloride compound powder particle used in the manufacture of the silver-silver chloride electrode of this invention.

For obtaining a stable electrode by the present invention, the proportion of silver chloride relative to silver must be at least 0.05% by weight. If it exceeds 80% by weight, an extremely large electrode potential will result, which is not desirable. The desirable range of the silver chloride proportion is between 40 and 50% by weight.

The silver powder particles should preferably have a purity higher than 99.9%, with an average particle size smaller than 250 mesh (Tyler mesh).

The manufacturing method of the silver-silver chloride electrode according to the present invention is to chemically react silver powder with chlorine either in a solution containing chlorine ions or in a gas mixture containing chlorine or a chlorine compound to form silver chloride in a quantity from 0.05 to 80%, followed by compression-forming the silver chloride into a desired shape, wherein formation of the silver chloride may be controlled by suitable selection of the chlorine concentration in the solution, concentration of the chlorine gas or chlorine compound gas (concentration in an inert gas such as nitrogen), treatment period and so on. A conventional cold-forming method may be employed for the compression-forming.

It is established that the silver-silver chloride electrode of the present invention is capable of a quick reversible redox reaction and is porous, allowing large surface areas with silver and silver chloride to be compactly arranged in a homogeneous mixture, so that it is superior to conventional electrodes with a shorter period of reaching stable electrode potential, smaller drift potential and further with excellent polarization characteristics. The manufacturing process is also superior in that it does not require the steps of weighing silver and silver chloride in an appropriate proportion, mixing, and heat treating as required in conventional methods. Thus, it is economically advantageous.

EXAMPLE 1

Silver powder of a purity higher than 99.9% (325 mesh) was soaked in 10% HCl to react with the chlorine ions, and under agitation it underwent the chemical reaction for 15 minutes to form silver chloride in a quantity of 0.05% by weight on the surface of the silver powder particles. The resultant silver-silver chloride compound powder was rinsed with water until pH value of rinsing water became 7, then dried at 110° C. About 0.35 g of this compound powder was weighed out and formed under a pressure of 0.5–3 ton/cm$^2$, into a porous electrode pellet of 8 mm in diameter and 1 mm in thickness. After connecting with a silver-plated lead wire with insulating coating, exposed portion of the lead wire was molded with polyethylene, and a silver-silver chloride electrode according to the present invention was obtained.

EXAMPLE 2

Silver powder of a purity higher than 99.9% (325 mesh) was soaked in 20% HCl to react with the chlorine ions, and under agitation it underwent the chemical reaction for 30 minutes to form silver chloride in a quantity of 40% by weight on the surface of the silver powder particles. The resultant silver-silver chloride compound powder was treated in the same manner as in Example 1 to make a silver-silver chloride electrode.

EXAMPLE 3

Silver powder of a purity higher than 99.9% (325 mesh) was soaked in 30% HCl to react with the chlorine ions, and under agitation it underwent the chemical reaction for 90 minutes to form silver chloride in a quantity of 80% by weight on the surface of the silver powder particles. The resultant silver-silver chloride compound powder was treated in the same manner as in Example 1 to make a silver-silver chloride electrode.

EXAMPLE 4

Silver powder of a purity higher than 99.9% (400 mesh) was reacted for 10 minutes under agitation with chlorine in a moist nitrogen gas containing 5 ppm chlorine gas for 10 minutes and 0.05% by weight of silver chloride was formed on the surface of the silver powder particles. The resultant silver-silver chloride compound powder material was treated under vacuum or in an inert gas to remove excessive chlorine gas. Weighing out 0.35 g of this compound powder, a porous electrode pellet of 8 mm in diameter and 1 mm in thickness was formed under a pressure 2 t/cm$^2$. A silver-plated lead wire with insulating coating was connected to the pellet, followed by sealing the exposed portion of the lead wire by molding to obtain a silver-silver chloride electrode.

EXAMPLE 5

Silver powder of a purity higher than 99.9% (400 mesh) was stirred in a nitrogen gas containing 500 ppm chlorine for 30 minutes to form 40% by weight of silver chloride on the surface of the silver powder particles. The resultant silver-silver chloride compound powder was treated in the same manner as in Example 4 to make a silver-silver chloride electrode.

EXAMPLE 6

Silver powder of a purity higher than 99.9% (400 mesh) was stirred in a nitrogen gas containing 6,000 ppm chlorine gas for 30 minutes, and 80% by weight of silver chloride was formed on the surface of the silver powder particles. The resultant silver-silver chloride compound powder was treated in the same manner as in Example 4 to make a silver-silver chloride electrode.

Figure 2:
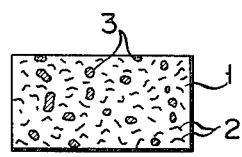
FIG. 2 shows the texture of an electrode pellet obtained by compression-forming the silver-silver chloride compound powder shown in FIG. 1.

FIG. 1 is an enlarged electron-microscopic sectional view representing a silver-silver chloride compound particle with a ragged surface obtained by forming silver chloride 2 on the surface of a silver particle 1. It was noted that the raggedness was more pronounced with more formation of silver chloride. The silver chloride covering the surface of the silver particle was broken by the compression-forming procedure and clean silver surfaces were exposed, so that the silver and silver chloride were compactly arranged in a uniform mixture. As shown in FIG. 2, it was confirmed that silver chloride 2 was uniformly distributed in a porous silver matrix 1 having voids 3.

Figure 3:
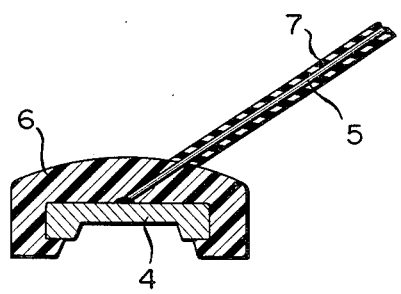
FIG. 3 is a sectional view showing a skin electrode obtained by connecting a lead wire to the electrode pellet of FIG. 2.

Each silver-silver chloride electrode obtained in each of the above examples was then measured for electrode characteristics by connecting a silver-plated lead wire 5 with an insulating layer 7 to an electrode pellet 4 and molding the exposed portion of the lead wire with polyethylene as shown in FIG. 3. In other words, the polarization potential (10 μA×5 seconds application), the electrode potential and the period for reaching a virtually constant electrode potential in an isotonic sodium chloride solution (20° C.), and the electrode potential drift 2–7 minutes after the submersion were measured. The results are presented in the following table. In the table, a comparative case is included wherein silver powder of a purity higher than 99.9% and silver chloride powder were weighed out in a proportion of 90 to 10 and mixed mechanically, followed by the same treatment as in Example 1, giving a conventional silver-silver chloride electrode. The standard electrode used is a saturated calomel electrode (SCE).

TABLE

| Electrode | Electrode potential mV (V vs SCE) | Stabilizing time min. | Drift potential μV/min. | Polarization potential mV (10μA × 5sec. applied) | Silver chloride % by weight |
|---|---|---|---|---|---|
| Example 1 | 36.4 | 4.0 | 200 | 0.7 | 0.05 |
| Example 2 | 34.7 | 0.5 | 20 | 1.2 | 40 |
| Example 3 | 34.0 | 3.5 | 60 | 3.8 | 80 |
| Example 4 | 38.0 | 4.0 | 250 | 1.0 | 0.05 |
| Example 5 | 33.9 | 1.5 | 30 | 1.5 | 40 |
| Example 6 | 34.5 | 3.5 | 80 | 5.0 | 80 |
| Comparative Example | 35.6 | 4.5 | 280 | 2.6 | 10 |

Although HCl solution was used in Examples 1–3 for reacting silver powder and chlorine ions, this should not be construed as a limitation but any solution that contain chlorine ions such as sodium hypochlorite may be used, and if necessary, a reaction accelerator such as hydrogen peroxide may also be added. Although chlorine gas was used in Examples 4–6 for chemically reacting silver powder and chlorine, this should not either be construed as a limitation but any chlorine gas compound such as HCl may be used.

We claim:

1. A silver-silver chloride electrode characterized in that said electrode is obtainable by forming silver chloride on the surface of silver powder particles in a proportion of 0.05 to 80% by weight and compression-forming the resultant compound powder.

2. A silver-silver chloride electrode according to claim 1 wherein the particle size of said silver powder is smaller than 250 mesh.

3. A silver-silver chloride electrode according to claim 1 wherein the weight proportion of said silver chloride is 40 to 50% by weight.

4. A method of manufacturing a silver-silver chloride electrode comprising the steps of chemically reacting silver powder particles with chlorine in a solution containing chlorine ions or in a gas mixture containing chlorine or a chlorine compound to form silver chloride on the surface of the silver powder particles, and compression-forming the resultant silver-silver chloride compound powder into a desired shape.

5. A method of manufacturing a silver-silver chloride electrode according to claim 4 wherein the proportion of said silver chloride formed on the surface of said silver powder particles is 0.05 to 80% by weight relative to said silver powder.

6. A method of manufacturing a silver-silver chloride electrode according to claim 5 wherein the particle size of said silver powder is smaller than 250 mesh.

7. A method of manufacturing a silver-silver chloride electrode according to claim 5 wherein said solution containing chlorine ions is either an aqueous HCl solution or aqueous solution of sodium hypochlorite.

8. A method of manufacturing a silver-silver chloride electrode according to claim 5 wherein said chlorine gas compound is HCl.

* * * * *